United States Patent
Fouillet et al.

(10) Patent No.: US 10,082,135 B2
(45) Date of Patent: Sep. 25, 2018

(54) METHOD FOR PRODUCING AT LEAST ONE DEFORMABLE MEMBRANE MICROPUMP AND DEFORMABLE MEMBRANE MICROPUMP

(75) Inventors: Yves Fouillet, Voreppe (FR); Francois Baleras, Saint Georges de Commiers (FR); Martine Cochet, Moirans (FR); Sandrine Maubert, Corenc (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 1101 days.

(21) Appl. No.: 13/508,650

(22) PCT Filed: Nov. 12, 2010

(86) PCT No.: PCT/EP2010/067390
§ 371 (c)(1),
(2), (4) Date: May 8, 2012

(87) PCT Pub. No.: WO2011/058140
PCT Pub. Date: May 19, 2011

(65) Prior Publication Data
US 2012/0224981 A1 Sep. 6, 2012

(30) Foreign Application Priority Data

Nov. 13, 2009 (FR) ...................... 09 57995

(51) Int. Cl.
*F04B 45/04* (2006.01)
*F04B 43/04* (2006.01)
(Continued)

(52) U.S. Cl.
CPC ....... *F04B 43/046* (2013.01); *A61M 5/14586* (2013.01); *B81C 1/00182* (2013.01);
(Continued)

(58) Field of Classification Search
CPC ...... F04B 43/046; F04B 43/043; F04B 43/02; F04B 45/047; F04B 53/10; F04B 53/16; A61M 5/14586; B81C 1/00182
(Continued)

(56) References Cited

U.S. PATENT DOCUMENTS 5,085,562 A 2/1992 Van Lintel
5,096,388 A * 3/1992 Weinberg .............. F04B 43/043
417/413.1
(Continued)

FOREIGN PATENT DOCUMENTS

DE 197 19 861 A1 11/1998
DE 103 34 240 A1 2/2005
(Continued)

OTHER PUBLICATIONS

U.S. Appl. No. 14/406,795, filed Dec. 10, 2014, Marchalot, et al.
(Continued)

*Primary Examiner* — Essama Omgba
*Assistant Examiner* — Connor Tremarche
(74) *Attorney, Agent, or Firm* — Oblon, McClelland, Maier & Neustadt, L.L.P.

(57) ABSTRACT

A method for producing at least one deformable membrane micropump including a first substrate and a second substrate assembled together, the first substrate including at least one cavity and the second substrate including at least one deformable membrane arranged facing the cavity. In the method: the cavity is produced in the first substrate; then the first and second substrates are assembled together; then the deformable membrane is produced in the second substrate.

7 Claims, 9 Drawing Sheets

(51) Int. Cl.
*F04B 43/02* (2006.01)
*A61M 5/145* (2006.01)
*B81C 1/00* (2006.01)

(52) U.S. Cl.
CPC .......... *F04B 43/02* (2013.01); *F04B 43/043* (2013.01); *B81B 2201/036* (2013.01); *B81B 2203/0127* (2013.01); *B81C 2201/019* (2013.01); *B81C 2201/0167* (2013.01); *F05C 2203/02* (2013.01); *F05C 2203/06* (2013.01); *Y10T 29/494* (2015.01)

(58) Field of Classification Search
USPC .......................................................... 417/53
See application file for complete search history.

(56) References Cited

U.S. PATENT DOCUMENTS

| | | | | |
|---|---|---|---|---|
| 5,224,843 | A * | 7/1993 | van Lintel | F04B 43/046 137/859 |
| 5,259,737 | A * | 11/1993 | Kamisuki | B81B 3/0005 257/E21.233 |
| 5,375,979 | A * | 12/1994 | Trah | F04B 19/24 417/207 |
| 5,585,011 | A | 12/1996 | Saaski et al. | |
| 5,617,632 | A | 4/1997 | Saaski et al. | |
| 5,660,728 | A | 8/1997 | Saaski et al. | |
| 5,697,153 | A | 12/1997 | Saaski et al. | |
| 5,702,618 | A | 12/1997 | Saaski et al. | |
| 5,705,070 | A | 1/1998 | Saaski et al. | |
| 5,839,467 | A | 11/1998 | Saaski et al. | |
| 5,883,420 | A * | 3/1999 | Mirza et al. | H01L 29/82 257/419 |
| 6,033,191 | A * | 3/2000 | Kamper | F04B 43/043 417/322 |
| 6,395,638 | B1 * | 5/2002 | Linnemann | F04B 43/043 417/413.1 |
| 6,991,214 | B2 * | 1/2006 | Richter | F15C 5/00 251/129.06 |
| 7,372,348 | B2 * | 5/2008 | Xu | F03G 7/065 200/181 |
| 2002/0096488 | A1 | 7/2002 | Gulvin et al. | |
| 2004/0036047 | A1 * | 2/2004 | Richter | F15C 5/00 251/129.06 |
| 2005/0123420 | A1 * | 6/2005 | Richter | F04B 43/046 417/413.2 |
| 2006/0186085 | A1 * | 8/2006 | Fuertsch | F04B 43/043 216/41 |
| 2008/0180491 | A1 * | 7/2008 | Sugahara | B41J 2/17509 347/70 |
| 2009/0130822 | A1 * | 5/2009 | Collet | B81C 1/0015 438/459 |
| 2013/0175171 | A1 | 7/2013 | Aizel et al. | |

FOREIGN PATENT DOCUMENTS

| | | |
|---|---|---|
| DE | 10 2005 042 656 A1 | 3/2007 |
| EP | 0 392 978 A1 | 10/1990 |
| EP | 0 465 229 A1 | 1/1992 |
| EP | 0 568 902 A2 | 11/1993 |
| EP | 1 226 944 A1 | 7/2002 |
| WO | WO 95/09987 | 4/1995 |

OTHER PUBLICATIONS

International Search Report dated Oct. 13, 2011, in PCT/EP2010/067390.

Nam-Trung Nguyen, et al., "MEMS-Micropumps: A Review", Journal of Fluids Engineering, Transactions of the ASME, vol. 124, Jun. 2002, pp. 384-392.

Nadim Maluf, et al., "An Introduction to Microelectromechanical Systems Engineering", Artech House, Inc., Second Edition, 2004, 7 pages.

Z. J. Pei, et al., "Grinding of silicon wafers: A review from historical perspectives", International Journal of Machine Tools & Manufacture, vol. 48, 2008, pp. 1297-1307.

Alexander F. Doll, et al., "A novel artificial sphincter prosthesis driven by a four-membrane silicon micropump", Sensors and Actuators A, vol. 139, 2007, pp. 203-209.

C. Malhaire, et al., "Design of a polysilicon-on-insulator pressure sensor with original polysilicon layout for harsh environment", Thin Solid Films, vol. 427, 2003, pp. 362-366.

* cited by examiner

METHOD FOR PRODUCING AT LEAST ONE DEFORMABLE MEMBRANE MICROPUMP AND DEFORMABLE MEMBRANE MICROPUMP

FIELD OF THE INVENTION

The present invention relates to the general field of microfluidics, and relates to a method for producing at least one deformable membrane micropump, and to a deformable membrane micropump.

STATE OF THE RELATED ART

Micropumps provide controlled flow of a fluid in a microchannel. They can be used in numerous microfluidic systems such as, for example, labs-on-a-chip, medical substance injection system or electronic chip hydraulic cooling circuits.

The fluid flow may be obtained in different ways, depending on whether mechanical action is performed on the fluid of interest or not. An overview of the various techniques can be found in the article by Nguyen et al. entitled "MEMS-Micropumps: A Review", 2002, J. Fluid. Eng., Vol. 124, 384-392.

Deformable membrane micropumps belong to the first category of micropumps wherein a mechanical action is applied to the fluid via said membrane, so as to displace the fluid in the microchannel.

The document US2005/0123420 describes an example of such a micropump comprising three deformable membranes, including one central pumping membrane and two upstream and downstream secondary membranes.

As illustrated in FIG. 1, the micropump 1 comprises a first substrate 10 and a second substrate 20 assembled together so as to form a microchannel.

The first substrate 10 comprises three cavities 12-1, 12-2, 12-3 formed in the top face 11S of the substrate and connected in series.

The second substrate 20 comprises three deformable membranes 22-1, 22-2, 22-3 arranged facing said cavities. It should be noted that the second substrate 20 is formed from a single piece, the deformable membranes thus being a portion of said substrate and not added parts.

The central membrane 22-2 and the corresponding cavity 12-2 define the pumping chamber of the micropump 1 together. The upstream 22-1 and downstream 22-3 membranes form, with the corresponding cavities 12-1 and 12-3 thereof, active valves.

The deformation of the membranes is obtained using piezoelectric chips 31 arranged on the top face 21S of the membranes.

The flow of the fluid of interest in the micropump microchannel is obtained by controlled deformation of the membrane increasing or decreasing the pumping chamber volume, in conjunction with the action of the upstream and downstream valves.

The method for producing such a micropump comprises a step for producing cavities and membranes, followed by a step for assembling said substrates.

The cavities and membranes are firstly produced, respectively, in the first and second substrates using conventional microelectronic techniques, for example, photolithography followed by one or a plurality of etching steps. It should be noted that the membranes of the second substrate generally have a thickness in the region of tens of microns.

The first and second substrates, when they are made of silicon, may then be assembled together by molecular bonding, also referred to as silicon direct bonding (SDB).

This assembly technique, known to those skilled in the art, is particularly described in the publication by Maluf and Williams entitled "An introduction to microelectromechanical systems engineering", Artech House, 2004.

It comprises a prior substrate face cleaning phase, followed by the alignment of the substrates and contacting with each other. The whole is then subjected to a high temperature, in the region of 1000° C., for a period ranging from several minutes to several hours.

However, this production method gives rise to a number of drawbacks, particularly with respect to the second substrate.

Indeed, the handling of the second substrate before and during the assembly step, particularly during the cleaning phase in the case of direct bonding, gives rise to high mechanical stress in the second substrate, particularly on the membranes due to the thinness thereof. The risks of membrane degradation (breakage, tearing, etc.) are thus high.

Therefore, to limit these risks, the second substrate is etched so as to have an embossed geometry. As shown in FIG. 1, the membranes 22-1, 22-2, 22-3 are formed by recesses produced in the top face 21S of the second substrate. The non-etched portions thus form thick portions, or ribs 25, separating the membranes from each other, and provide, due to the thickness and arrangement thereof, the rigidity required of the substrate.

However, the presence of the ribs in the top face of the second substrate inhibits the completion of subsequent photolithography steps in that it is not possible to deposit photosensitive resin with a spinner.

Moreover, during the subsequent deposition of dielectric or metallic layers on the top face of the second substrate, continuity problems arise due to the significant variations in height induced by the presence of the ribs.

Finally, it should be noted that these various drawbacks are particularly significant when the method relates to the simultaneous production of a plurality of micropumps using plates forming the first and second substrates. Indeed, these plates generally have a diameter in the region of one hundred millimeters for a thickness, as regards the wafer forming the second substrate, in the region of tens of microns on the membranes. It is understood that this aspect ratio renders the wafer forming the second substrate particularly fragile during the handling thereof before and during assembly.

DESCRIPTION OF THE INVENTION

The aim of the invention is that of providing a method for producing at least one deformable membrane micropump comprising two substrates assembled together, for limiting, before and during the step for assembling said substrates, the risks of degradation of the substrates, particularly of the substrate to comprise the deformable membrane(s).

For this purpose, the invention relates to a method for producing at least one deformable membrane micropump comprising a first substrate and a second substrate assembled together, the first substrate comprising at least one cavity and the second substrate comprising at least one deformable membrane arranged facing said cavity, said first and second substrates defining a portion of a microchannel together wherein said cavity and said deformable membrane are situated. Said method comprises the following steps:

said cavity is produced in the first substrate, then said deformable membrane is produced in the second substrate, and the first and second substrates are assembled together.

According to the invention, the step for producing the deformable membrane is performed after the assembly step.

Both substrates are thus assembled together before the step for producing the deformable membrane. The second substrate, before and during the assembly step, does not comprise a deformable membrane, thus a localized fragile zone.

Therefore, before and during the assembly step, the risks of degradation (breakage, rupture, splitting, etc.) of the substrates in general and of the second substrate in particular, due to excessive mechanical stress generated during handling, are substantially reduced in relation to the risks present in the method according to the prior described above.

Furthermore, the choice of assembly technique to use is no longer limited. Unlike the prior art, it is possible to choose an assembly technique from those in which the operating conditions, particularly in terms of pressure and temperature, subject the substrates to high mechanical and thermal stress. Due to the lack of a deformable membrane during the assembly step, the risks of degradation of the second substrate are substantially reduced, or negligible.

Said second substrate comprises a top face and a bottom face, said substrate being assembled with said first substrate on the bottom face thereof. Advantageously, the step for producing said deformable membrane is performed by thinning said second substrate from the top face thereof, said thinning being performed by mechanical polishing, chemical mechanical polishing and/or etching.

Preferably, the second substrate, comprising said deformable membrane, is produced from a single piece. Therefore, said deformable membrane is not an added element rigidly connected to the second substrate but a structural part of said second substrate.

Said assembly step may be performed by molecular bonding, anodic, eutectic bonding or by gluing. Preferably, the assembly step is performed by molecular bonding. This technique is sometimes referred to as silicon direct bonding (SDB).

Preferably, the first substrate comprises a conduit communicating with the first cavity, a subsequent thinning step by etching at least one portion of said first substrate being made from the bottom face thereof, so as to render said conduit a through conduit.

Said assembly step is advantageously performed in a vacuum. In this way, if the microchannel portion forms a closed volume sealed by the second substrate, it is possible to apply a high temperature without risking giving rise to the thermal expansion of gases present in said volume. This expansion would give rise to high mechanical stress in said substrate which would weaken the assembly in particular.

Advantageously, following the step for producing said deformable membrane, the second substrate has a substantially plane top face on the entire surface thereof.

Therefore, unlike the prior art, microelectronic methods conventionally performed on plane surfaces may be performed on the top face of the second substrate. These methods may comprise subsequent deposition, particularly of photosensitive resin, with a spinner, photolithography and etching steps.

A plurality of micropumps can be produced simultaneously from said first and second substrates, said first and second substrates being respectively formed from a single piece.

Said production method may comprise a final step for separating said previously produced micropumps from each other.

The invention also relates to a deformable membrane micropump comprising a first substrate and a second substrate assembled with each other, the first substrate comprising at least one cavity and the second substrate comprising at least one deformable membrane arranged facing said cavity, said first and second substrates defining a portion of a microchannel together wherein said cavity and said deformable membrane are situated.

According to the invention, said second substrate has, along said microchannel portion, a substantially constant thickness.

The term substantially constant thickness refers to a thickness in which the value is liable to display local variations less than or equal to 10% of the maximum value thereof in the zone in question, and preferably less than or equal to 5%, or 1%.

Said second substrate comprises a top face and a bottom face, said substrate being assembled with said first substrate on the bottom face thereof.

Advantageously, the second substrate has a substantially plane top face on the entire surface thereof.

Said deformable membrane may have a thickness less than or equal to 300 µm, and preferably less than 100 µm, or less than 50 µm.

Said first and second substrates are, preferably, made of silicone, silicon-on-insulator (SOI), or glass. Preferably, the first substrate is made of silicon and the second substrate is made of SOI.

Said first substrate may comprise at least one boss arranged in said cavity facing the deformable membrane, forming an abutment for said membrane. In this way, during the production of the membrane, the second substrate may be subject, due to the technique used, to strain causing deflection towards the first substrate. The presence of the boss thus makes it possible to limit deflection by forming an abutment for the second substrate. The mechanical stress associated with the deflection is thus likewise limited.

Advantageously, the first substrate comprises a second cavity and the second substrate comprises a second deformable membrane arranged facing said second cavity, said second cavity and said second deformable membrane being situated within said microchannel portion, said first substrate comprising a conduit opening inside the second cavity via an opening bordered by a lip projecting inside said second cavity, parallel with said second deformable membrane.

The term lip refers to a projecting rigid rib.

Preferably, said lip and said second deformable membrane comprise, in relation to each other, a gap between 0.01 µm and 3 µm. Preferably, said gap is between 0.01 µm and 3 µm.

In this way, in the case of an assembly technique during which a high temperature is applied, there is no risk of thermal deformation of either of the substrates. It is thus possible to produce particularly small gaps between a particular zone of the first substrate and a particular zone of the second substrate.

Advantageously, a stressed layer is arranged on the top face of the second substrate facing a deformable membrane, such that said membrane is deformed in an idle position.

Advantageously, a strain gage is arranged on the top face of the second substrate facing a deformable membrane, so as to measure a deformation of said membrane.

Further advantages and features of the invention will emerge in the non-limitative detailed description hereinafter.

BRIEF DESCRIPTION OF FIGURES

Embodiments of the invention will now be described, as non-limitative examples, with reference to the appended figures, wherein.

DETAILED DESCRIPTION OF A PREFERRED EMBODIMENT

The production method described hereinafter is applied to a micropump comprising three deformable membranes, but may also be applied to any type of deformable membrane micropump such as those, for example, comprising at least one deformable membrane and check valves or converging conduits arranged upstream and downstream from said membrane. The method may be applied to a micropump comprising n membranes according to the invention, where n is greater than or equal to 1, and preferably equal to 3. When n is equal to 1, the method leads to the creation of an active valve, the membrane being arranged between an inlet conduit and an outlet conduit.

Furthermore, the method is described with reference to the production of a single micropump, but may be applied to the simultaneous production of a plurality of micropumps.

FIGS. 2A to 2E illustrate, in a cross-section, a deformable membrane micropump, for various steps of the production method according to the preferred embodiment.

It should be noted that the scales are not observed, for improved clarity of the figure.

Figure 2A:
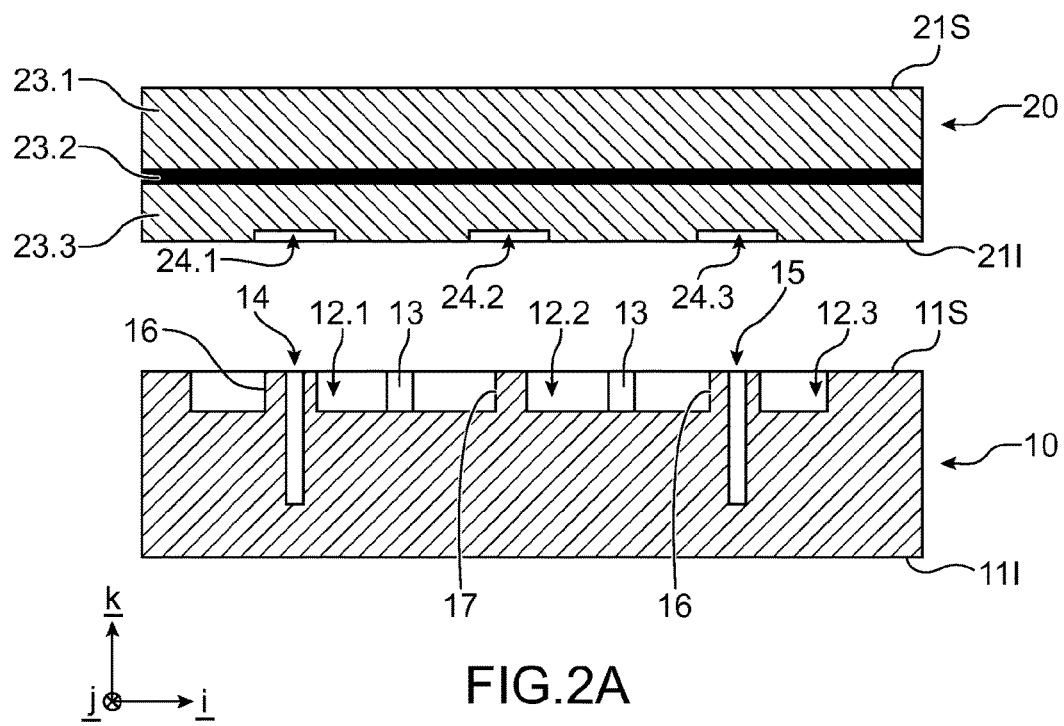
FIG. 2A to 2E are cross-sectional views of a deformable membrane micropump, for various steps of the production method according to the invention.

Throughout the description hereinafter, an orthonormal point (i,j,k), represented in FIG. 2A, is used.

Moreover, the terms "bottom" and "top" used hereinafter are in this case to be understood in terms of orientation along the direction k of the orthonormal point (i,j,k) represented in FIG. 2A.

The terms "thickness", "height" and "depth" are to be understood in terms of distance along the direction k of said orthonormal point (i,j,k).

A first substrate 10 formed, for example, from a double-faced polished silicon wafer is taken into consideration.

A second substrate 20 formed, for example, from a silicon-on-insulator wafer (SOI) is taken into consideration. A layer of $SiO_2$ 23-2 is thus present between two top 23-1 and bottom 23-3 silicon layers.

The thickness of the first and second substrates is in the region of a few hundred microns, for example 700 µm.

The diameter or the diagonal of the first and second substrates may be in the region of a few millimeters to tens of centimeters, for example 10, 15, 20 or 30 cm. In the case of simultaneous production of a plurality of micropumps, the substrates may have a diameter or a diagonal in the region of tens of centimeters. The micropumps obtained following the production method may form, for example a rectangle measurement 1 cm by 3 cm.

The thickness of the bottom silicon layer 23-3 of the second substrate 20 is substantially equal to the thickness of the deformable membranes subsequently produced. This thickness may thus be in the region of tens to hundreds of microns, for example 10 µm to 300 µm, and preferably less than 100 µm, or less than 50 µm. As detailed below, the bottom layer 23-3 of the second substrate makes it possible to define the thickness of the deformable membranes to be produced with precision.

According to a first step of the method, a plurality of cavities 12-1, 12-2, 12-3 are produced in the top face 11S of the first substrate 10, along with communication conduits 13.

The term cavity refers to a recess or a notch produced in the surface of a solid.

Three cavities 12-1, 12-2, 12-3 are thus obtained, one central cavity 12-2 and two upstream 12-1 and downstream 12-3 cavities, connected in series via communication conduits 13. The central cavity 12-2 helps form the pumping chamber and the two upstream 12-1 and downstream 12-3 cavities help form active valves.

The cavities 12-1, 12-2, 12-3 may have the form of a disk, ring, polygon, or any other shape of the same type, having a diameter or diagonal of a few millimeters, for example 3 mm or 6 mm, and a depth in the region of a few microns to hundreds of microns, for example 50 µm to 100 µm. Indeed, a compression rate, corresponding to the ratio between the volume of fluid displaced by the membrane and the volume of the cavity situated facing the membrane, may be defined. It is preferable for this compression rate to be as high as possible. In addition, the depth of a cavity is preferably less than or equal to 100 µm.

Inlet 14 and outlet 15 conduits are produced in the form of wells opening, respectively, inside, respectively, upstream 12-1 and downstream 12-3 cavities, but, preferably, not fully through with respect to the first substrate 10. They may be situated at the center of said cavities. They may have a diameter in the region of hundreds of microns, for example 600 µm, and a depth in the region of hundreds of microns, for example 300 µm.

The inlet 14 and outlet conduits open into said cavities via an orifice bordered by an annular lip 16. The lips 16 may have a height substantially equal to the depth of the cavities wherein they are situated.

In this case, undercuts 24-1, 24-3 are produced in the bottom face 21I of the second substrate 20, intended to face the corresponding lips 16. Said undercuts may thus be annular or have the shape of a disk, and are shallow, in the region of a few microns, for example 2 µm, or tenths of a micron, for example 0.1 µm.

The term undercut refers to a shallow recess or notch, typically between 0.1 µm and 3 µm, facing that of the cavities, in the region of tens of microns, for example 50 or 100 µm. The bottom face 21I of the second substrate 20 can thus be considered to be substantially plane. The term "substantially" in this instance refers to variations in thickness in said substrate not exceeding a few microns, for example 3 µm.

These undercuts 24-1, 24-3 make it possible to ensure, during the subsequent substrate assembly step, that the top of lips 16 does not touch the bottom face 21I of the second substrate 20. Furthermore, these undercuts 24-1, 24-3 will also provide fluidic communication, in the case of a membrane not subject to mechanical stress, between the inlet 14 and outlet 15 conduits and the cavities 12-1, 12-3 wherein they open.

Moreover, a boss 17 may be produced in the top face 11S of the first substrate 10 and located substantially at the center of the central cavity 12-2. To prevent contact between the bottom face 21I of the second substrate 20 and the top of the boss 17, a undercut 24-2 is advantageously produced in the bottom face 21I.

Figure 3:
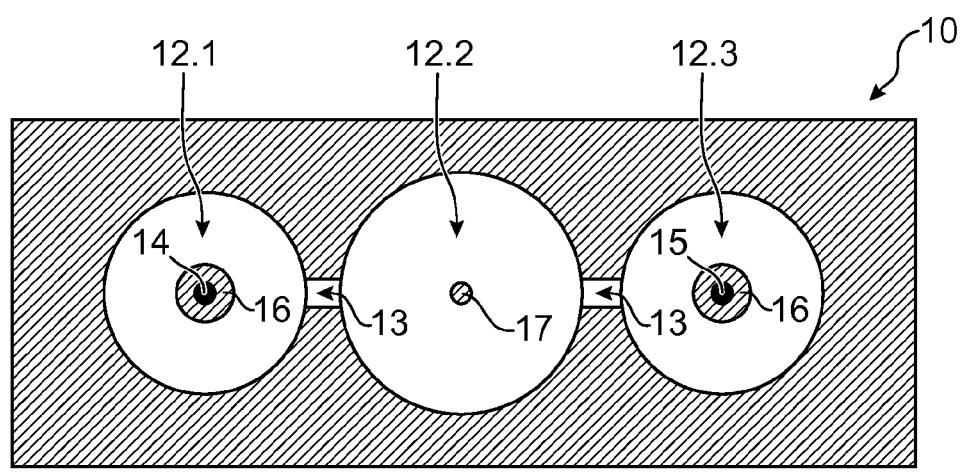
FIG. 3 is a top view of the first substrate, after the step for producing cavities and before the assembly step.

The production of the cavities 12-1, 12-2, 12-3, communication conduits 13 and inlet 14 and outlet 15 conduits in the first substrate 10 (represented as a top view in FIG. 3) and undercuts 24-1, 24-2, 24-3 in the second substrate 30 may be performed using conventional microelectronic techniques, for example photolithography followed by some etching steps. The etching may be performed using RIE (Reactive Ion Etching) plasma, making it possible to obtain vertical walls. The term "vertical" means oriented along the vector k of the point (i,j,k).

In an alternative embodiment, it is possible not to produce undercuts in the bottom face 21I of the second substrate 20, which remains plane. The height of the lips 16 is thus less than the depth of the upstream 12-1 and downstream 12-3 cavities wherein they are situated. During the subsequent substrate assembly step, the top of the lips 16 does not touch the bottom face 21I of the second substrate. Furthermore, the fluidic communication, in the case of a membrane not subject to mechanical stress, between the inlet 14 and outlet 15 conduits and the cavities 12-1, 12-3 wherein they open is also provided. Similarly, it is possible to produce a boss 17 wherein the height is less than the depth of the central cavity 12-2 wherein it is situated.

According to a second step of the method, said substrates are then assembled together.

According to the preferred embodiment, the first and second substrates 10, 20 being respectively made of silicon and SOI, it is possible to perform assembly by molecular bonding. This type of bonding is particularly suitable for Si—Si or Si-glass type assemblies. This technique is also referred to as fusion bonding, or direct bonding.

This molecular bonding assembly step comprises a first phase for preparing the faces of the substrates 10, 20 to be assembled, more specifically cleaning and hydration.

The substrates 10, 20 are thus cleaned by means of a wet treatment such as RCA cleaning, particularly described in the publication cited above by Maluf and Williams entitled "An introduction to microelectromechanical systems engineering". This cleaning technique makes it possible to obtain clean and uncontaminated surfaces, having a high OH group density.

Figure 2B:
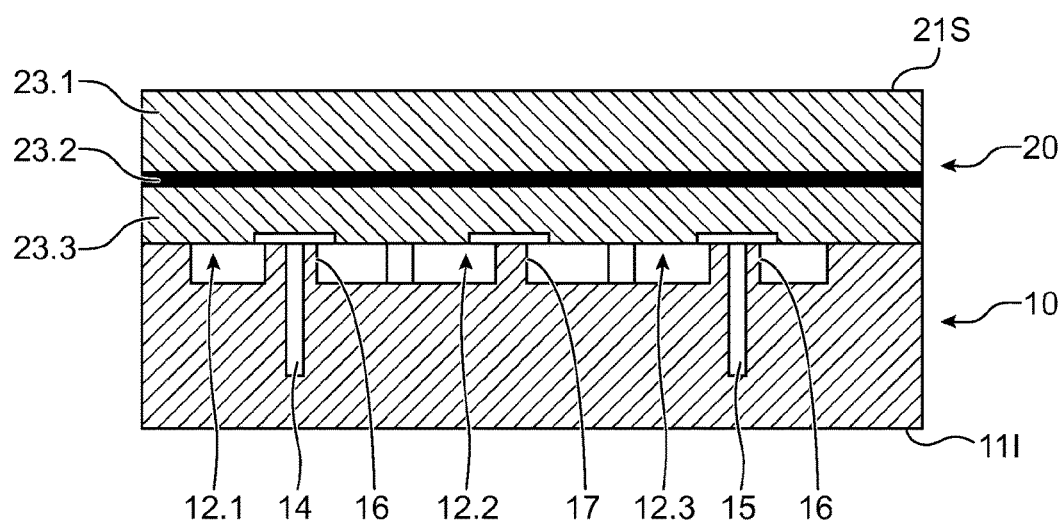

As shown in FIG. 2B, the substrates are then aligned and contacted with each other.

Finally, high-temperature bonding annealing is performed for a predetermined time. The temperature may be between 500° C. and 1250° C., for example in the region of 1000° C. and the annealing time may be in the region of one hour. The substrate assembly obtained is thus resistant and durable.

The assembly of both substrates may also be carried out using other methods such as gluing, or eutectic bonding or anodic bonding.

It is understood that, during the assembly step, the second substrate 20 has not yet undergone a deformable membrane production step. The thickness of the second substrate 20 is thus substantially identical to the initial thickness thereof, i.e. hundreds of microns. The undercuts optionally produced 24-1, 24-2, 24-3 in the bottom face 21I have a negligible depth in relation to the total thickness of the second substrate 20, and thus do not change the overall rigidity of the substrate 20. Therefore, the handling of the second substrate 20 before and during the assembly step involves low risks of degradation due to breaking or tearing.

Moreover, the first and second substrates 10, 20 have a sufficient thickness rendering any deformation negligible during bonding, particularly as said bonding is preferentially performed in a vacuum. The gap between the top of the lips 16 of the first substrate 10 and the bottom face 21I of the second substrate 20 may thus be very small, for example in the region of a micron or a tenth of a micron as mentioned above. Therefore, there is no risk that, following thermal deformation of either of the substrates, the lips 16 and the bottom face 21I of the second substrate 20 are mutually contacted such that bonding of said surfaces takes place. For the same reason, the gap between the top of the boss 17 and the bottom face 21I may also be in the region of a micron or a tenth of a micron.

Alternatively to said undercuts, or combined therewith, it is possible to perform a surface treatment inhibiting bonding locally between the top of the lips 16 and the boss 17 and the bottom face 21I of the second substrate 20. This surface treatment, preferably performed on the bottom 21I of the second substrate on the surface facing said lips 16 and boss 17, may be a micro-machining producing rough surface condition, the deposition of a hydrophobic material or having a low adhesion strength, or a chemical surface treatment or ion implantation.

Finally, it should be noted that, during this assembly step, the inlet 14 and outlet 15 conduits may not be through, as shown in FIGS. 2A and 2B. In this case, the assembly step is advantageously performed in a vacuum. The ambient pressure may be, for example, between a few $10^{-4}$ mbar and a few $10^{-2}$ mbar. This makes it possible avoid that, by means of thermal expansion of gases trapped in the closed volume formed by the cavities 12-1, 12-2, 12-3 and conduits 13, 14, 15, significant pressure surges do not give rise to excessive mechanical stress inside said substrates, but also in the assembly zone between the two substrates.

According to the third step of the method, deformable membranes are finally produced in the second substrate.

Figure 2C:
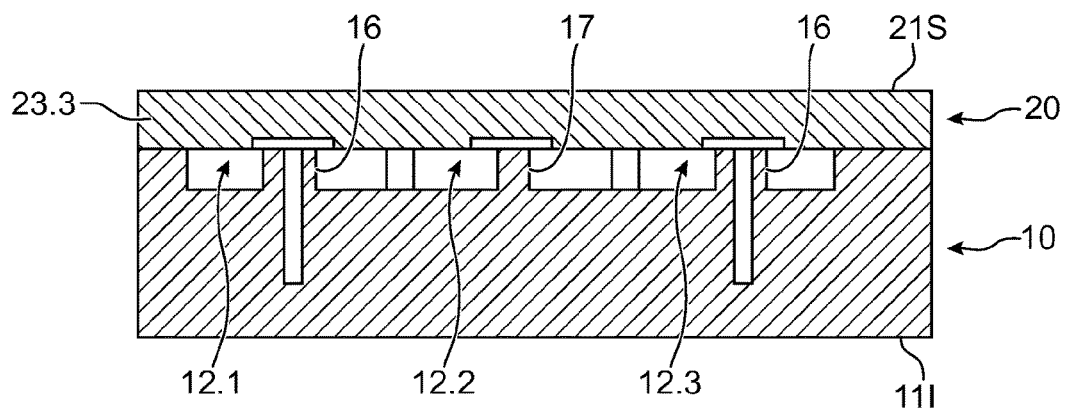

As shown in FIGS. 2B and 2C, this embodiment may be carried out by thinning the second substrate 20 on the entire surface thereof, from the top face 21S thereof.

A first mechanical polishing phase such as grinding may be performed. This technique is particularly described in the article by Pei et al. entitled "Grinding of silicon wafers: A review from historical perspectives", Int. J. Mach. Tool. Manu., 48 (2008), 1297-1307.

The polishing may be stopped a few microns or tens of microns above the intermediate $SiO_2$ layer 23-2.

The thinning to the intermediate layer 23-2 may be obtained by the known chemical mechanical polishing (CMP) technique. Alternatively or in combination with this technique, RIE dry etching and/or wet etching by means of a KOH or IMAM (tetramethylammonium hydroxide) bath may be performed. In the case of dry or wet etching, the SiO₂ layer offers the advantage of serving as a barrier layer, making it possible to control the final thickness of the membrane to be formed with precision.

Finally, the intermediate SiO₂ layer 23-2 of the second substrate 20 may be etched by means of RIE (Reactive Ion Etching) dry etching or hydrofluoric acid (HF) etching or by any known reduction means.

As illustrated in FIG. 2C, the second substrate 20 has a substantially plane top face 21S and essentially comprises the bottom layer 23-3 of the initial SOI.

This thus results in a second substrate wherein the top face 21S is substantially plane, and wherein the thickness is substantially homogenous. The term "substantially" covers any variations in thickness in the region of 0.1 μm to 3 μm from undercuts 24-1 to 24-3 produced on the bottom face 21I of the second substrate 20.

According to this embodiment, the second substrate 20 does not have geometrically defined zones for forming deformable membranes. Due to the thickness thereof, in the region of tens to hundreds of microns, for example 10 μm to 300 μm, and preferably 50 μm, any zone in the second substrate is liable to form a deformable membrane when it is positioned facing a cavity produced in the bottom substrate. Nevertheless, the zones of the second substrate 20 situated facing the cavities 12-1, 12-2, 12-3 are intended to form deformable membranes 22-1, 22-2, 22-3.

It should be noted that the thinning step may be performed at atmospheric pressure while the cavities are still forming a closed volume in a vacuum. A pressure force is then applied on the top face 21S of the second substrate 20, tending to cause flexion thereof inside the cavities 12-1, 12-2, 12-3. Advantageously, the boss 17 arranged in the central cavity 12-2 forms an abutment for the second substrate 20 and thus applies a limit to the flexural deflection thereof. The lips 16 situated in the upstream 12-1 and downstream 12-3 cavities may also form an abutment for the second substrate 20 and also help limit the maximum possible flexion of the second substrate.

Moreover, subsequent steps may be performed to finalize the production of the deformable membrane micropump.

Due to the absence of projecting ribs in the top face 21S of the second substrate 20, it is possible to perform, on this face, conventional micro-production steps such as steps consisting of deposition, photolithography by means of photosensitive resin deposition with a spinner, and etching.

Figure 2D:
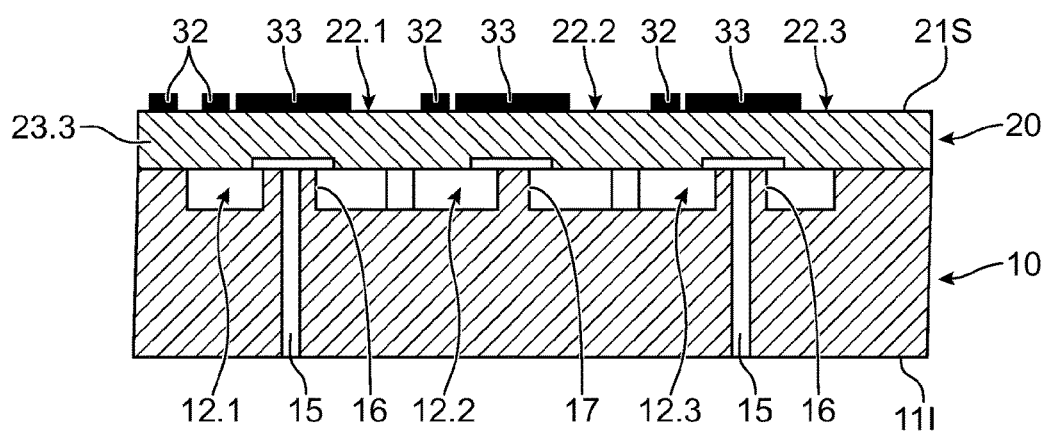

As shown in FIG. 2D, a conductive level may be produced on the top face 21S of the second substrate 20. This conductive level is produced by depositing a metallic layer, for example gold, aluminum, titanium, platinum, alloy (e.g. AlSi), etc. Any type of conductive material deposition available in clean rooms may be suitable.

A dielectric passivation layer (not shown) may then be deposited on the faces of the micropump. The material may be SiO₂, SiN, Si₃N₄ having a thickness of a few nanometers. This layer provides the protection and local isolation of the conductive layer.

The conductive layer and the passivation layer may then be etched locally to form conductive tracks and electrical power supply zones of the deformable membrane actuation means.

The membrane actuation means may be piezoelectric chips. The layers are then etched to form contact blocks 32 for providing the electrical power supply of the micropump with the external system, conductive disks 33 for receiving the piezoelectric chips and conductive tracks for connecting the contact blocks with the conductive disks.

The conductive disks 33 have a diameter substantially equal to that of the piezoelectric chips. This diameter may be in the region of 0.5 to 0.85 times the diameter of the cavities facing which the disks are arranged.

Figure 2E:
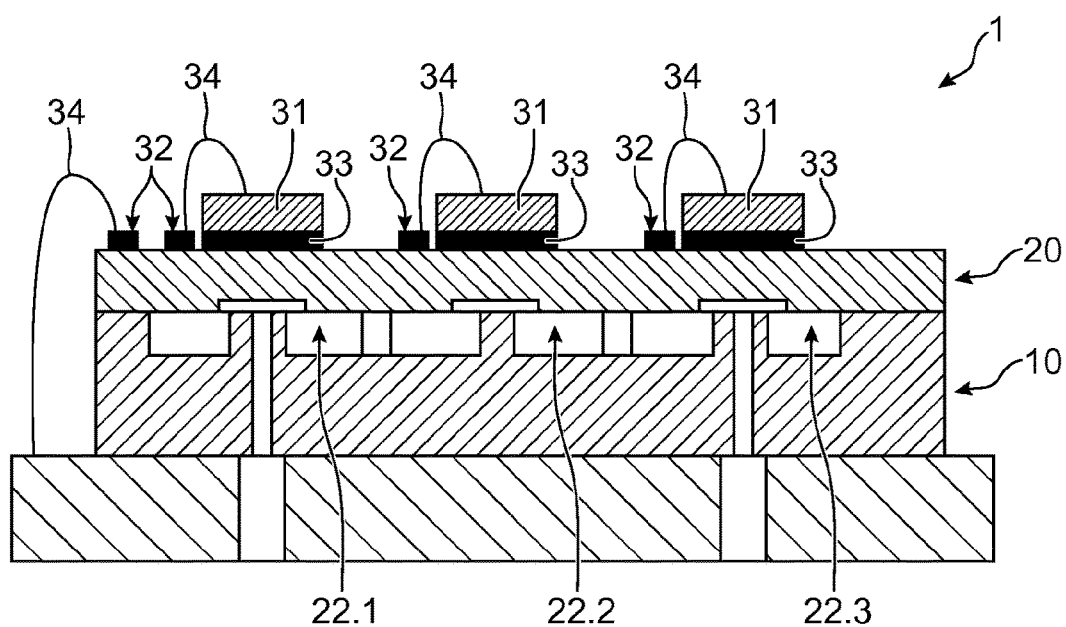

As shown in FIG. 2E, chips 31 are then produced on the top face 21S of the second substrate 20, and arranged on the deformable membranes 22-1, 22-2, 22-3. They each rest on a conductive disk 33 and are assembled therewith using a conductive adhesive. The thickness of the piezoelectric chips may be in the region of one hundred microns, for example 125 μm to 200 μm. An overview of the piezoelectric materials suitable for use can be found in the article by Doll et al. entitled "A novel artificial sphincter prosthesis driven by a four-membrane silicon micropump", Sensor. Actuat. A-Phys., 2007, Vol. 139, 203-209.

Alternatively, the chips may be obtained after chemical vapor deposition (CVD) or sol-gel deposition. In this case, the thickness of the chips may be less than 1 μm or a few microns.

Finally, an electric wire 34 is welded to the top face of the piezoelectric chips and connected to the conductive tracks. An electric voltage may thus be applied, independently, to each piezoelectric chip. The deformation of a piezoelectric chip thus gives rise to the deformation of the corresponding deformable membrane. The piezoelectric chips may this be used as membrane actuation means to deform said membranes. It should be noted that they may also be used as a sensor for measuring the membrane movement, or the position thereof induced by deformation.

In the preferred embodiment of the method according to the invention, the inlet 14 and outlet 15 conduits are not fully through. An etching step, optionally with photolithography, is then performed on the bottom face 11I of the first substrate 10 to render said conduits through. The micropump microchannel, formed from the inlet 14 and outlet 15 conduits, cavities 12-1, 12-2, 12-3 and communication conduits 13, is thus open and communicates with the external environment.

This step is advantageously performed following the production method. This makes it possible to prevent contamination inside the micropump microchannel by all sorts of residue or impurities. The risk of blockage or poor operation of the upstream and downstream valves is thus ruled out.

Finally, if a plurality of micropumps is produced simultaneously from a wafer forming the first substrate and a second wafer forming the second substrate, the wafers are cut to separate the micropumps produced.

Figure 4:
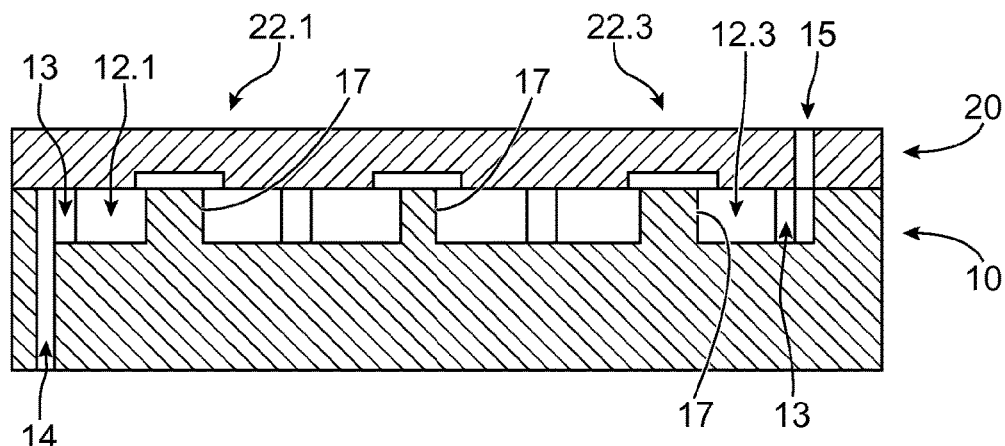
FIG. 4 is a longitudinal sectional view of an alternative embodiment of a micropump according to the invention, wherein the inlet and outlet conduits are particularly arranged outside the upstream and downstream cavities.
Figure 5:
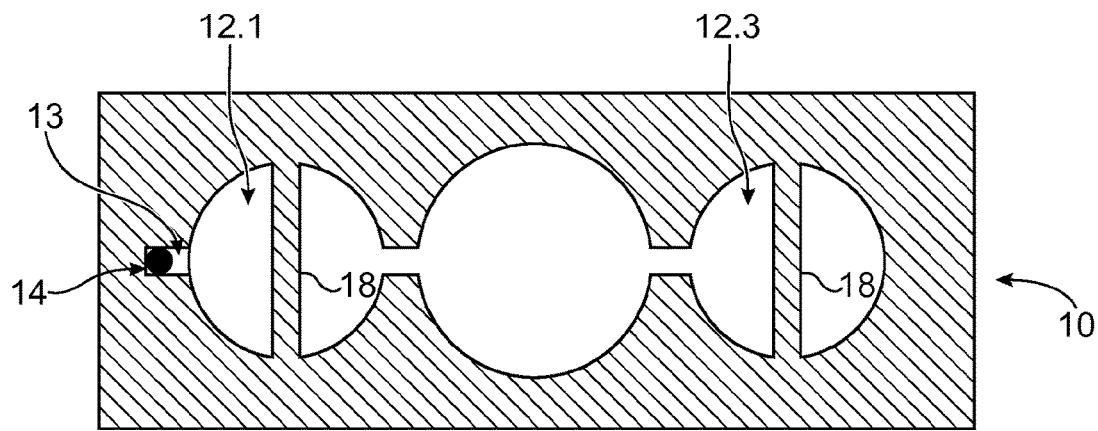
FIG. 5 is a top view of the first substrate as represented in FIG. 4.

FIGS. 4 and 5 illustrate an alternative embodiment of a micropump wherein the inlet and outlet conduits are located outside the upstream and downstream cavities.

The identical numeric references to those in FIGS. 2A to 2E refer to identical or similar elements.

The inlet 14 and outlet 15 conduits are in this case arranged substantially adjacent to the upstream 12-1 and downstream 12-3 cavities and communicate therewith via communication conduits 13.

According to FIG. 4, the inlet conduit extends inside the first substrate whereas the outlet conduit extends inside the second substrate. This arrangement is given herein merely as an example. It is obviously possible to arrange the inlet conduit in the second substrate and the outlet conduit in the first substrate, or arrange said conduits inside the second substrate.

As shown in FIG. 5, to act as an active valve, each lip may be replaced by a straight (or curved) rib 18 extending inside the corresponding cavity 12-1, 12-3 and formed in said first substrate 10. The corresponding membrane 22-1, 22-3 may then come into contact with the rib 18 in order to prevent any flow of the fluid of interest between the rib and the membrane.

In an alternative embodiment of the preferred embodiment described above, a stressed layer may be deposited directly on the surface on the top face of either of the membranes produced, before the deposition of the conductive layer. This stressed layer applies a stress on the membrane in question giving rise to deformation thereof. For example, this stressed layer may be deposited on the upstream and downstream membranes and thus gives rise to the contacting of the membranes with the opposite lips. Therefore, when the membranes are not activated by the actuation means, in this case by piezoelectric chips, the membranes are deformed in an idle position. They thus form upstream and downstream valves which are closed when idle.

Figure 6:
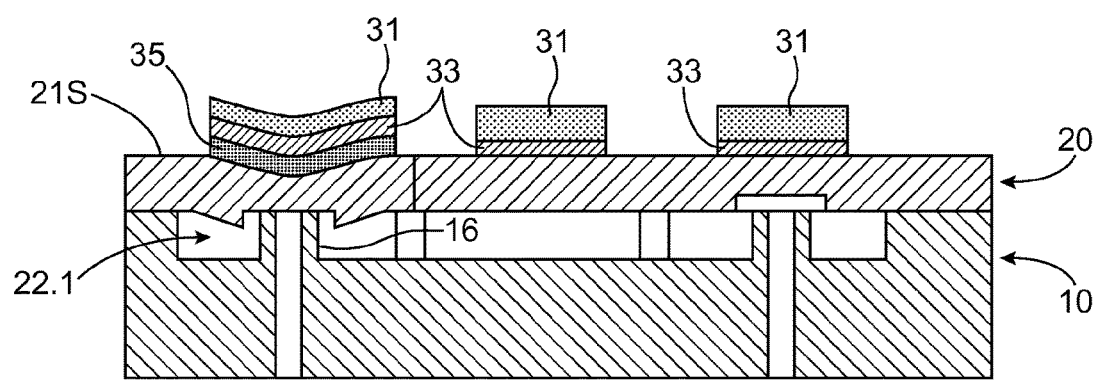
FIG. 6 is a longitudinal sectional view of an alternative embodiment of a micropump according to the invention, wherein a stressed layer is arranged on a membrane of the second substrate.

This stressed layer may be, for example, Si3N3 deposited by PECVD having an internal tensile stress in the region of several hundred Megapascal, for example 700 MPa. The thickness thereof may be in the region of 0.1 μm to 1 μm. As illustrated in FIG. 6, the deflection of the membrane 22-1 induced by the stressed layer 35 is thus a few microns and is sufficient to induce the contacting of the membrane with the opposite lip 16.

In an alternative embodiment, strain gages may be produced on the top face of the second substrate and arranged above the deformable membranes. These gages are used to measure the deformation of the membrane to determine the position thereof (high, low or intermediate position), measure the local pressures in the micropump microchannel. For example, it is possible to measure the difference in pressure between the upstream cavity and the downstream cavity, and thus measure the fluid flow rate or detect a leak.

The strain gages may be made of a conductive material have a high gage factors, for example metal, such as platinum, or preferably, a doped semi-conductor material such as, for example p-doped silicon obtained by boron ion implantation. Boron ion implantation may be performed directly on the Si membrane.

It is also possible to produce a Wheatstone bridge with four gages having opposing measurement directions. Such a bridge is particularly described in the article by Malhaire and Barbier entitled "Design of a polysilicon-on-insulator pressure sensor with original polysilicon layout for harsh environment", 2003, Thin Solid Films, 427, 362-366.

Figure 7:
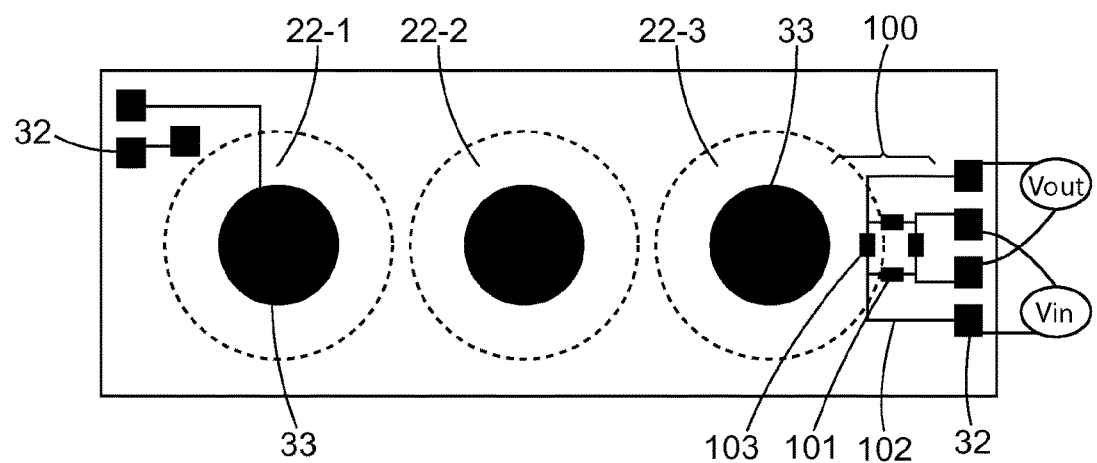
FIG. 7 is a top view of an alternative embodiment of a micropump according to the invention comprising a deformation membrane sensor.

An example of an integrated sensor 100 is given in FIG. 7 corresponding to the top view drawing of a pump similar to the one described on FIG. 6. The sensor 100 and the electrical elements 32 are formed by at least one electrical level, typically a metallic layer as described above in reference to FIG. 2D. The metallic disks 33, blocks 32 and the various electrical lines, and the sensor 100, may be formed in the same metallic material and shaped by a single step such as deposition, photolithography, etching. A much more complex embodiment integrating a plurality of electrical levels may also be envisaged. For example, doped silicon piezoelectric resistors may also be envisaged.

In the example in FIG. 7, the material is a 100 nm to 500 nm gold layer deposited by means of standard microtechnology methods. The sensor is formed from a Wheatstone bridge having four piezoresistive resistances 101 having an identical geometry. For example, the resistors 101 are formed from a coil a few microns (e.g., between 3 and 10 μm) wide and approximately 1 mm long. Lines 102 connected to the block 32 are used to power the bridge and make the measurement. One of the resistors 103 is positioned facing the membrane 22-3. Preferably, the resistor 103 is positioned at the embodiment of the membrane 22-3, so as to be located in the stress and maximum deformation zone when the membrane is deformed. The three other resistors of the Wheatstone bride are situated outside the membrane so as to retain a constant resistance value regardless of the membrane deformation state. The membrane 22-3 is deformed under the action of a pressure difference between the two faces of the membrane and/or under the effect of the actuation of the piezoelectric chip. These deformations give rise to a change in the value of the resistor 103 due to the piezoresistive effect. This change in the resistor is measured precisely by the electrical measurements on the Wheatstone bridge (known to those skilled in the art). For example, the bridge is powered with a voltage $V_{in}$ of 1 V, and the voltage $V_{out}$ is measured as shown in FIGS. 7 and 8.

Figure 8:
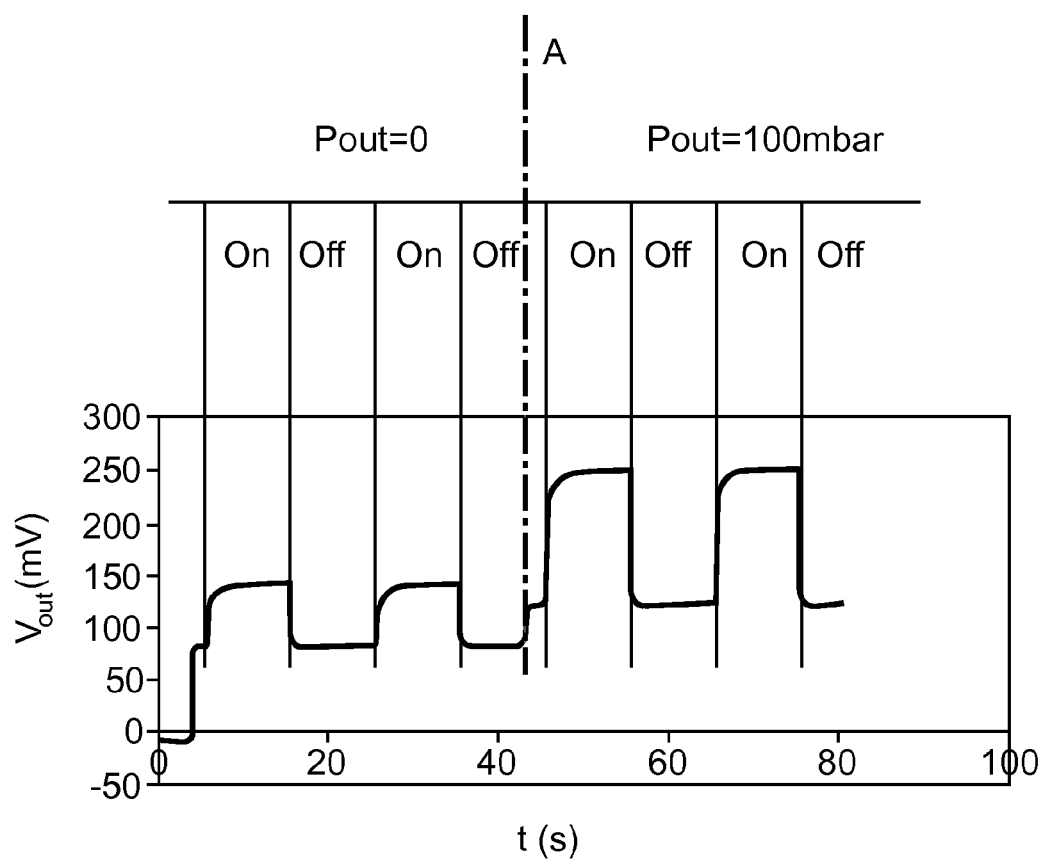
FIG. 8 shows the evolution of an output signal of the sensor represented in FIG. 7.

An example of a result is given in FIG. 8. The curve gives the progression of the voltage measurement $V_{out}$. A change in the value of this voltage measurement results from bridge disequilibrium and is thus directly correlated with the membrane deformation (position). More specifically, the piezoelectric chip mounted on the membrane 22-3 is actuated by an electrical signal in the form of square pulses. In FIG. 8, the On-Off indication designates the ranges in which the piezoelectric chip is actuated or is idle, respectively. It is verified that the actuation cycles are clearly visible on the sensor measurement curve. The change of membrane status can thus be verified, qualified and quantified readily using electrical means. The sensor thus makes it possible to verify the satisfactory behavior of the membrane during pump operation. It is also possible to determine the membrane deformation amplitude (the deformation amplitude is practically proportional to the voltage applied on the piezoelectric chip).

Secondly (reference A in FIG. 8), a pressure of 100 mbar is applied at the pump outlet. This pressure ($P_{out}$) changes suddenly from 0 to 100 mbar. This change is clearly visible on the sensor signal recorded in FIG. 8. This demonstrates that the sensor can be used to verify the satisfactory operation of the pump, but also to measure the pump outlet pressure. The sensor is used to detect the blocking of the fluid path downstream from the pump, or more generally to measure the hydraulic impedance of the system at the pump outlet. Obviously, the same sensors may be positioned on the two other membranes 22-1, 22-2. With one sensor on the membrane at the pump inlet, pressure measurements may be made upstream from the pump.

Figure 1:
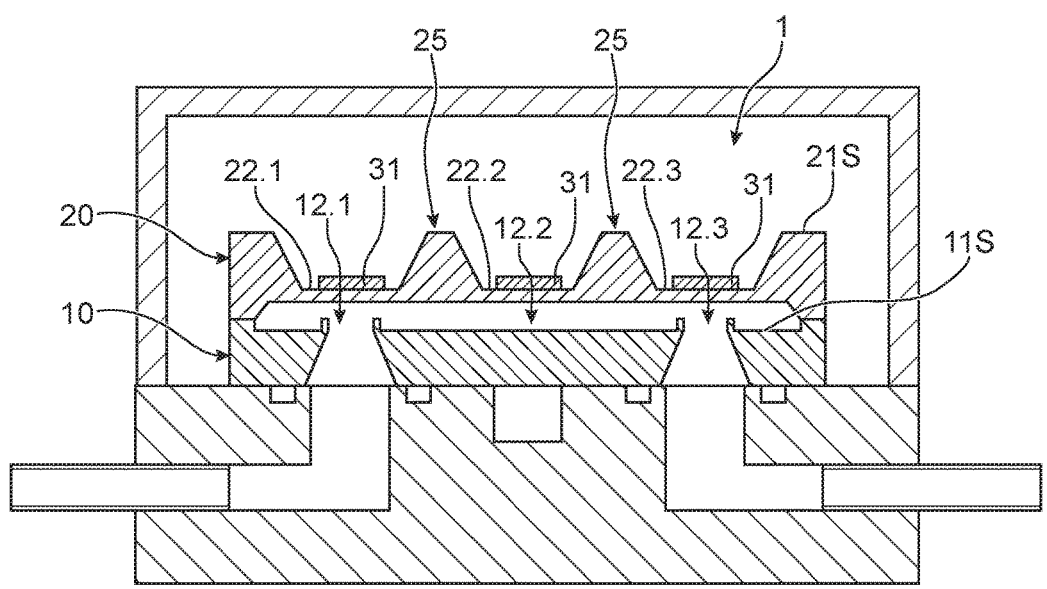
FIG. 1, described above, is a cross-sectional view of a deformable membrane micropump according to an example of the prior art.

The production of the sensors requires relatively fine resolutions (1 to 10 μm drawings for example). Moreover, the sensors should be positioned precisely in clearly defined zones of the membranes. If the top face of the pump is embossed (FIG. 1) according to the prior art, the production of such sensors is not possible. To produce these sensors by means of photolithography, it is essential for the top face of the pump to be plane. This demonstrates the benefit of the present invention, and illustrates the added value of the use of MEMS technologies on a pump produced according to the invention.

In an alternative embodiment of the preferred embodiment described above, a plurality of bosses forming an abutment may be produced and arranged in the upstream and/or downstream central cavities, or in the communication conduits. As described above, these bosses limit the deflection of the membranes during production in said corresponding cavities during the second substrate thinning step. They may also help, more generally, reinforce the micropump structure.

The height of the bosses may be equal to the depth of the corresponding cavities, in which case a undercut is produced in the bottom face of the second substrate and arranged facing each of said bosses. Alternatively, the height of the bosses may be substantially less than the depth of the corresponding cavities, with a difference in the region of microns or tenths of microns. The undercuts are not necessary in this case.

In an alternative embodiment, the first and second substrates may be made of silicon or glass. If the substrates consist of one made of silicon (or SOI) and another made of glass, it is possible to perform the step for assembling said substrates together using the known anodic bonding technique.

Moreover, the cavities, membranes and piezoelectric chips may have a circular shape, as described above. They may also have any other shape, for example oval, square, polygonal.

It should also be noted that the central membrane may have a different size to that of the upstream and downstream membranes. The size of the corresponding cavities is adapted accordingly. Thus, as an illustration, the pumping chamber may have a size of approximately 6 mm whereas the upstream and downstream chambers may have a size of 3 mm.

In an alternative embodiment of the embodiment of the method described above, the second substrate may be thinned from the top face thereof, not on the entire surface thereof, but only on a portion of said surface. For example, the second substrate of each micropump may have, on the top face thereof, a rib arranged on the border thereof and defining a substantially plane central surface.

Obviously, various modifications may be made by those skilled in the art to the invention described above, merely as non-limitative examples.

The deformable membrane micropump described above comprises active valves formed each comprising a deformable membrane. However, the invention may comprise, alternatively to the upstream and downstream membrane valves, check valves and converging conduits.

Finally, further types of membrane actuation are feasible, for example known pneumatic, magnetic, or electrostatic actuation methods.

The invention claimed is:

1. A method for producing at least one deformable membrane micropump including a first substrate and a separate second substrate that are assembled together, the first substrate including at least one cavity and the second substrate including at least one deformable membrane arranged facing the cavity, the first and second substrates defining a portion of a microchannel together wherein the cavity and the deformable membrane are situated, the method comprising:
   producing the cavity in the first substrate;
   producing a conduit in the cavity, the conduit being surrounded by an annular lip;
   producing an undercut in the second substrate on a bottom face of the second substrate that faces the first substrate, the undercut aligning with the conduit;
   subsequent to producing the cavity, the conduit, and the undercut, assembling together the first and second substrates to define the portion of the microchannel, the portion of the microchannel being enclosed by the first and second substrates; and
   producing the deformable membrane on the second substrate after the first and second substrates are assembled together,
   wherein the second substrate includes a layer of silicon dioxide sandwiched between two layers of silicon, and the second substrate is continuous over an entire length of the first substrate.

2. A method according to claim 1, wherein the second substrate includes a top face and the bottom face, the second substrate being assembled with the first substrate on the bottom face thereof, wherein the producing the deformable membrane is performed by thinning the second substrate from the top face thereof, the thinning being performed by mechanical polishing, chemical mechanical polishing, and/or etching.

3. A method according to claim 1, wherein the assembling is performed by molecular bonding, anodic, eutectic bonding, or by gluing.

4. A method according to claim 1, further comprising thinning by etching at least one portion of the first substrate from a bottom face thereof, so as to render the conduit a through conduit.

5. A method according to claim 4, wherein the assembling is performed in a vacuum.

6. A method according to claim 1, wherein, following the producing the deformable membrane, the second substrate has a substantially plane top face on an entire surface thereof.

7. A method according to claim 6, wherein subsequent deposition, photolithography, and etching are performed on the top face of the second substrate.

* * * * *